(12) United States Patent
Drobnik et al.

(10) Patent No.: US 6,989,543 B2
(45) Date of Patent: Jan. 24, 2006

(54) RADIATION SHIELDING CONTAINER FOR RADIOACTIVE SOURCES

(75) Inventors: Christopher D. Drobnik, Wauconda, IL (US); Michael W. Drobnik, Downers Grove, IL (US); Breese Watson, Chicago, IL (US); Kevin Wineinger, Aurora, IL (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/642,048

(22) Filed: Aug. 15, 2003

(65) Prior Publication Data

US 2005/0035310 A1   Feb. 17, 2005

(51) Int. Cl.
A61M 36/00 (2006.01)
A61N 5/00 (2006.01)
H01J 37/20 (2006.01)

(52) U.S. Cl. ............................ 250/455.11; 250/453.11; 600/7; 600/1

(58) Field of Classification Search .................... 600/7, 600/1, 2; 250/505.1, 506.1, 455.11, 453.11; 206/365; 53/449; 128/217
See application file for complete search history.

(56) References Cited

U.S. PATENT DOCUMENTS

| | | | |
|---|---|---|---|
| 1,576,535 A | | 3/1926 | Muir |
| 2,400,722 A | * | 5/1946 | Swan ........................ 206/210 |
| 2,860,635 A | * | 11/1958 | Wilburn ..................... 604/190 |
| 2,915,640 A | | 12/1959 | Grubel et al. |
| 3,256,441 A | | 6/1966 | Grasty |
| 3,369,121 A | | 2/1968 | Bruno et al. |
| 3,770,964 A | | 11/1973 | Backus |
| 3,882,315 A | | 5/1975 | Soldan |
| 4,020,355 A | | 4/1977 | Czaplinski et al. |
| 4,081,688 A | | 3/1978 | Fries |
| 4,501,360 A | | 2/1985 | Levy et al. |
| 4,510,924 A | * | 4/1985 | Gray ......................... 424/1.61 |
| 4,673,813 A | | 6/1987 | Sanchez |
| 4,697,575 A | * | 10/1987 | Horowitz ....................... 600/8 |
| 4,759,345 A | | 7/1988 | Mistry |
| 4,783,309 A | | 11/1988 | Popp et al. |
| 4,788,438 A | | 11/1988 | Evers |
| 4,846,235 A | | 7/1989 | Handke |
| 4,847,505 A | | 7/1989 | Suthanthiran |
| 4,863,023 A | | 9/1989 | Payne et al. |
| 4,872,563 A | | 10/1989 | Warder et al. |
| 4,923,088 A | | 5/1990 | Tanaka et al. |
| 4,972,087 A | | 11/1990 | Neider et al. |

(Continued)

FOREIGN PATENT DOCUMENTS

DE    3516838    11/1986

(Continued)

OTHER PUBLICATIONS

U.S. Appl. No. 09/728,603, filed Aug. 23, 2001, Gluschke et al.

(Continued)

Primary Examiner—John R. Lee
Assistant Examiner—Kalimah Fernandez
(74) Attorney, Agent, or Firm—Patti & Brill, LLC

(57) ABSTRACT

An apparatus in one example comprises a radiation shielding container for one or more radioactive sources. One or more of the one or more radioactive sources are containable within one or more cartridges. The radiation shielding container comprises a support component that restrains movement within the radiation shielding container of one or more of the one or more cartridges. The radiation shielding container comprises one or more vents for movement of a sterilant therethrough.

62 Claims, 6 Drawing Sheets

U.S. PATENT DOCUMENTS

| | | | |
|---|---|---|---|
| 4,997,090 A | | 3/1991 | Lenmark, Sr. et al. |
| 5,274,239 A | | 12/1993 | Lane et al. |
| 5,303,836 A | | 4/1994 | Childress |
| 5,346,096 A | | 9/1994 | Diersch et al. |
| 5,395,339 A | * | 3/1995 | Talonn et al. ............... 604/111 |
| 5,460,592 A | * | 10/1995 | Langton et al. ............... 600/7 |
| 5,519,931 A | | 5/1996 | Reich |
| 5,536,945 A | | 7/1996 | Reich |
| 5,552,612 A | | 9/1996 | Katayama et al. |
| 5,611,429 A | * | 3/1997 | Phillips .................. 206/365 |
| 5,672,883 A | | 9/1997 | Reich |
| 5,829,594 A | | 11/1998 | Warder |
| 5,834,788 A | | 11/1998 | Fu et al. |
| 5,894,134 A | | 4/1999 | Kissinger |
| 5,944,190 A | | 8/1999 | Edelen |
| RE36,693 E | | 5/2000 | Reich |
| 6,064,710 A | | 5/2000 | Singh |
| 6,084,243 A | | 7/2000 | Smith, Jr. et al. |
| 6,106,455 A | * | 8/2000 | Kan ........................... 600/7 |
| 6,108,392 A | | 8/2000 | Yoshizawa et al. |
| 6,113,529 A | | 9/2000 | Shi |
| 6,114,710 A | | 9/2000 | Contrepois et al. |
| 6,132,358 A | * | 10/2000 | Glenn et al. ............... 600/3 |
| 6,221,003 B1 | * | 4/2001 | Sierocuk et al. ............ 600/7 |
| 6,256,363 B1 | | 7/2001 | Methling et al. |
| 6,323,501 B1 | | 11/2001 | White et al. |
| 6,357,589 B2 | * | 3/2002 | Schmidt et al. ........... 206/364 |
| 6,366,633 B1 | | 4/2002 | Stezaly et al. |
| 6,425,174 B1 | | 7/2002 | Reich |
| 6,472,675 B2 | | 10/2002 | White et al. |
| 6,489,623 B1 | | 12/2002 | Peters et al. |
| 6,530,875 B1 | * | 3/2003 | Taylor et al. ............... 600/7 |
| 6,531,705 B2 | | 3/2003 | White et al. |
| 6,538,259 B2 | | 3/2003 | Matsunaga et al. |
| 6,572,527 B2 | * | 6/2003 | Steele et al. ............... 600/7 |
| 6,576,918 B1 | | 7/2003 | Fu et al. |
| 6,585,633 B2 | * | 7/2003 | Vitali et al. ............... 600/7 |
| 6,586,758 B2 | | 7/2003 | Martin |
| 6,592,508 B1 | * | 7/2003 | Ravins et al. ............... 600/8 |
| 6,629,960 B2 | * | 10/2003 | Fontayne ............... 604/240 |
| 2003/0028068 A1 | * | 2/2003 | Steele et al. ............... 600/7 |
| 2003/0045769 A1 | | 3/2003 | Kalas et al. |
| 2004/0084340 A1 | * | 5/2004 | Morelle et al. ............ 206/365 |

FOREIGN PATENT DOCUMENTS

| | | |
|---|---|---|
| DE | 4004037 | 5/1991 |
| EP | 0049439 | 4/1982 |
| EP | 0091175 | 10/1983 |
| EP | 405241 | 1/1991 |
| EP | 1 072 287 | 1/2001 |
| EP | 1076340 | 2/2001 |
| GB | 2024694 | 1/1980 |
| GB | 2163084 | 2/1986 |
| JP | 2264900 | 10/1990 |
| JP | 3099744 | 4/1991 |
| WO | WO 03/063944 | 8/2003 |

OTHER PUBLICATIONS

U.S. Appl. No. 10/194,607, filed Dec. 5, 2002, Reich.

U.S. Appl. No. 10/008,372, filed May 8, 2003, Pedersen et al.

MICK Radio-Nuclear Instruments, Inc., Prostate Accessories, Aug. 13, 2003, 3 pgs., Mick Radio Nuclear Instruments, Inc., Mount Vernon, USA.

Mick Radio-Nuclear Instruments, Inc., Prostate Accessories, Aug. 13, 2003, 2 pgs., Mick Radio-Nuclear Instruments, Inc., Mount Vernon, USA.

Standard Imaging, Inc., Mick Magazine Sterilizer, Aug. 1999, 7 pgs., Standard Imaging, Inc., Middletown USA.

* cited by examiner

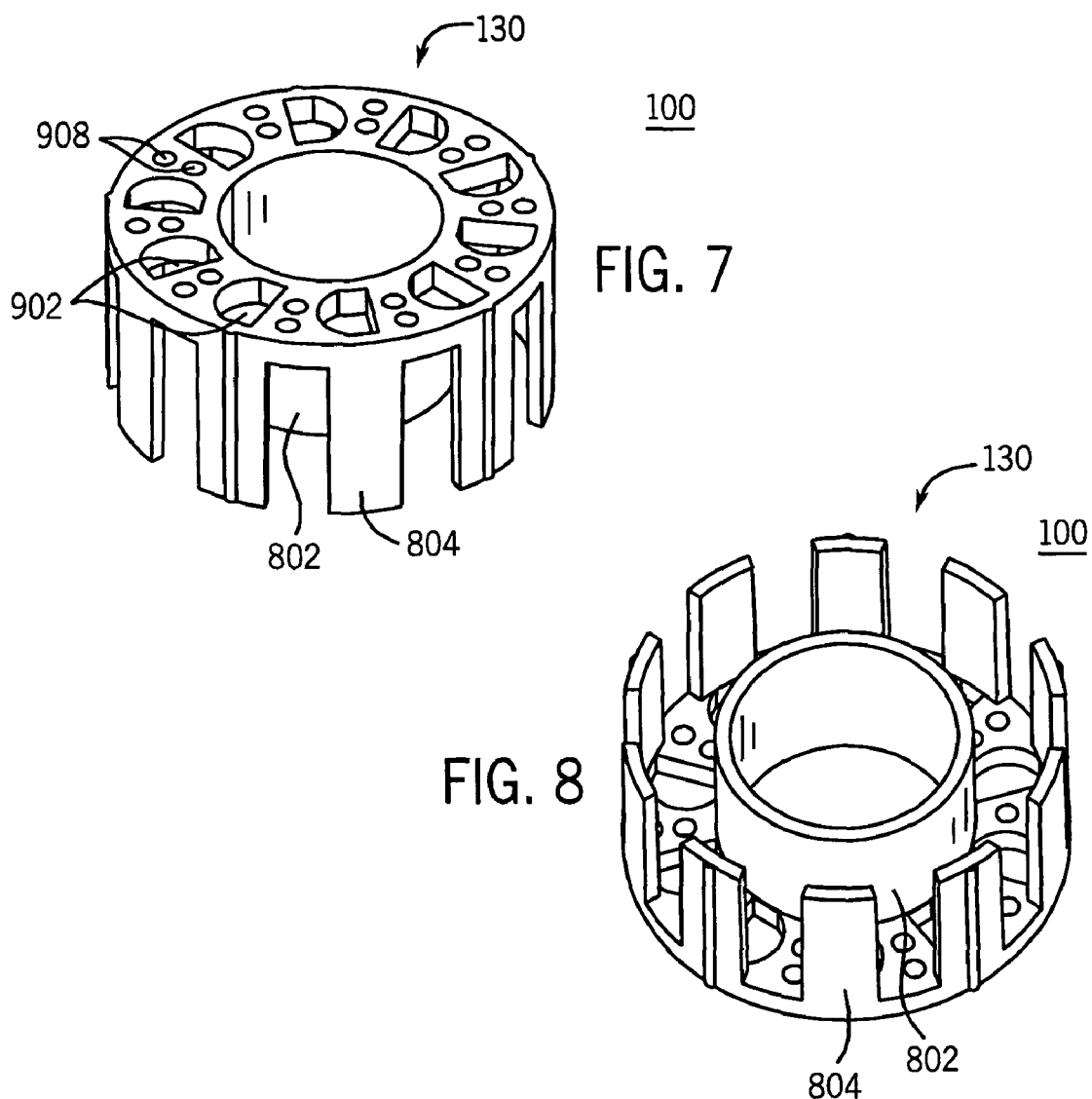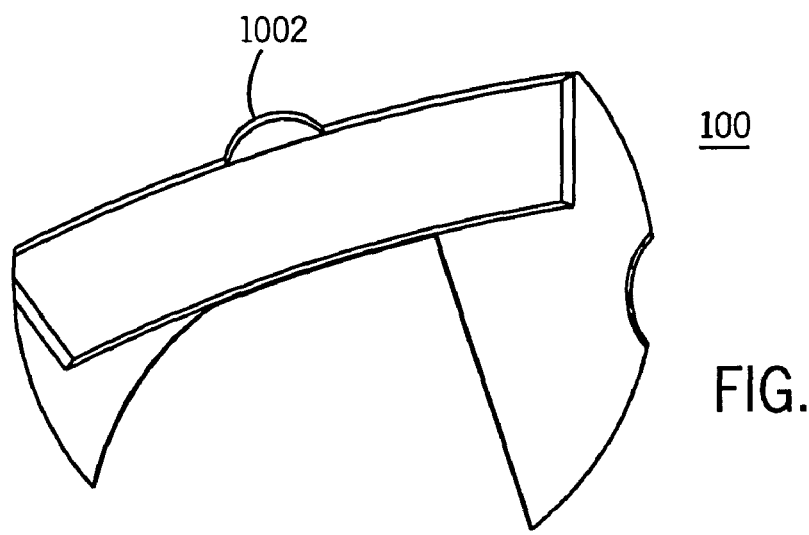

RADIATION SHIELDING CONTAINER FOR RADIOACTIVE SOURCES

TECHNICAL FIELD

The invention relates generally to shielding containers and more particularly to radiation shielding containers for radioactive sources.

BACKGROUND

Bodily cancers are commonly treated using radiation therapy. Radiation therapy employs high energy radiation to kill cancer cells. One type of radiation therapy is brachytherapy, in which a source of radiation is in direct contact with an afflicted tissue. A common brachytherapy treatment, transperineal seed implantation, involves placing radioactive seeds in the prostate gland to kill prostate gland cancer cells. A physician employs tools, for example, ultrasound, computerized axial tomography ("CAT") scans, and X-ray images in concert with dose-planning computer software programs to evaluate the medical condition of a patient. The physician constructs an optimal treatment plan to evenly distribute radiation throughout the afflicted tissue. Radioactive seeds of discrete radioactive strengths are inserted into the afflicted tissue through multiple implantation needles at positions corresponding to the treatment plan.

The physician in one example employs a radioactive seed applicator to insert the radioactive seeds into the afflicted tissue. The radioactive seed applicator engages with a radioactive seed cartridge. The radioactive seed cartridge holds one or more radioactive seeds. The radioactive seed cartridge transfers radioactive seeds from the radioactive seed cartridge to the radioactive seed applicator for insertion into the afflicted tissue. In one example, the physician loads the radioactive seed cartridge with the radioactive seeds just before use of the radioactive seed cartridge with the radioactive seed applicator. In another example, the physician receives the radioactive seed cartridge in a radiation shielding container with the radioactive seed cartridge pre-loaded with the radioactive seeds.

The radiation shielding container in one example is made from lead or steel to shield the physician from radiation of the radioactive seeds. The radiation shielding container fully encapsulates the radioactive seeds of the radioactive seed cartridge. The physician in one example opens the radiation shielding container and removes the radioactive seed cartridge from the radiation shielding container. The physician then places the radioactive seed cartridge in an autoclave for sterilization of the radioactive seeds. The radioactive seeds are not shielded during the time period between the physician removing the radioactive seed cartridge from the radiation shielding container and the physician placing the radioactive seed cartridge in the autoclave. As one shortcoming, the physician is exposed to radiation from the radioactive seeds during sterilization of the radioactive seeds.

Thus, a need exists for a radiation shielding container that promotes a reduction in exposure to radiation by the physician during sterilization of the radioactive seeds.

SUMMARY

The invention in one implementation encompasses an apparatus. The apparatus comprises a radiation shielding container for one or more radioactive sources. One or more of the one or more radioactive sources are containable within one or more cartridges. The radiation shielding container comprises a support component that restrains movement within the radiation shielding container of one or more of the one or more cartridges. The radiation shielding container comprises one or more vents for movement of a sterilant therethrough.

Another implementation of the invention encompasses an apparatus. The apparatus comprises a radiation shielding container for one or more radioactive seed cartridges. The radiation shielding container comprises a support component. The support component comprises one or more openings to receive the one or more radioactive seed cartridges. The radiation shielding container comprises an internal chamber that contains the support component and the one or more radioactive seed cartridges. The one or more radioactive seed cartridges within the radiation shielding container are able to be sterilized in an autoclave. The radiation shielding container comprises one or more passages that cause steam from the autoclave to follow one or more tortuous paths into the radiation shielding container to sterilize the one or more radioactive seed cartridges within the internal chamber.

Yet another implementation of the invention encompasses a radiation shielding container for one or more radioactive sources. The radiation shielding container comprises means for restraining movement within the radiation shielding container of one or more cartridges that hold one or more of the one or more radioactive sources. The radiation shielding container comprises means for allowing passage of sterilant into the radiation shielding container.

A further implementation of the invention encompasses a method. One or more cartridges that hold one or more radioactive sources are shipped in a radiation shielding container that comprises one or more vents for movement of a sterilant therethrough for sterilization of the one or more radioactive sources.

A still further implementation of the invention encompasses a method. A radiation shielding shipping container of one or more cartridges that hold one or more radioactive sources is received. The radiation shielding shipping container comprises one or more vents for movement of a sterilant therethrough. The one or more radioactive sources are sterilized within the radiation shielding shipping container by passing the sterilant into the radiation shielding shipping container through one or more of the one or more vents.

DESCRIPTION OF THE DRAWINGS

Features of exemplary implementations of the invention will become apparent from the description, the claims, and the accompanying drawings in which:

FIG. 7 is a top, perspective representation of the support component that restrains movement of one or more of the one or more radioactive sources within the radiation shielding container of the apparatus of FIG. 1.

FIG. 8 is a bottom, perspective representation of the support component of the radiation shielding container of the apparatus of FIG. 7.

FIG. 10 is a magnified representation of the protruding rib of the support component directed at the region of FIG. 9 indicated by reference numeral 10.

DETAILED DESCRIPTION

Figure 1:
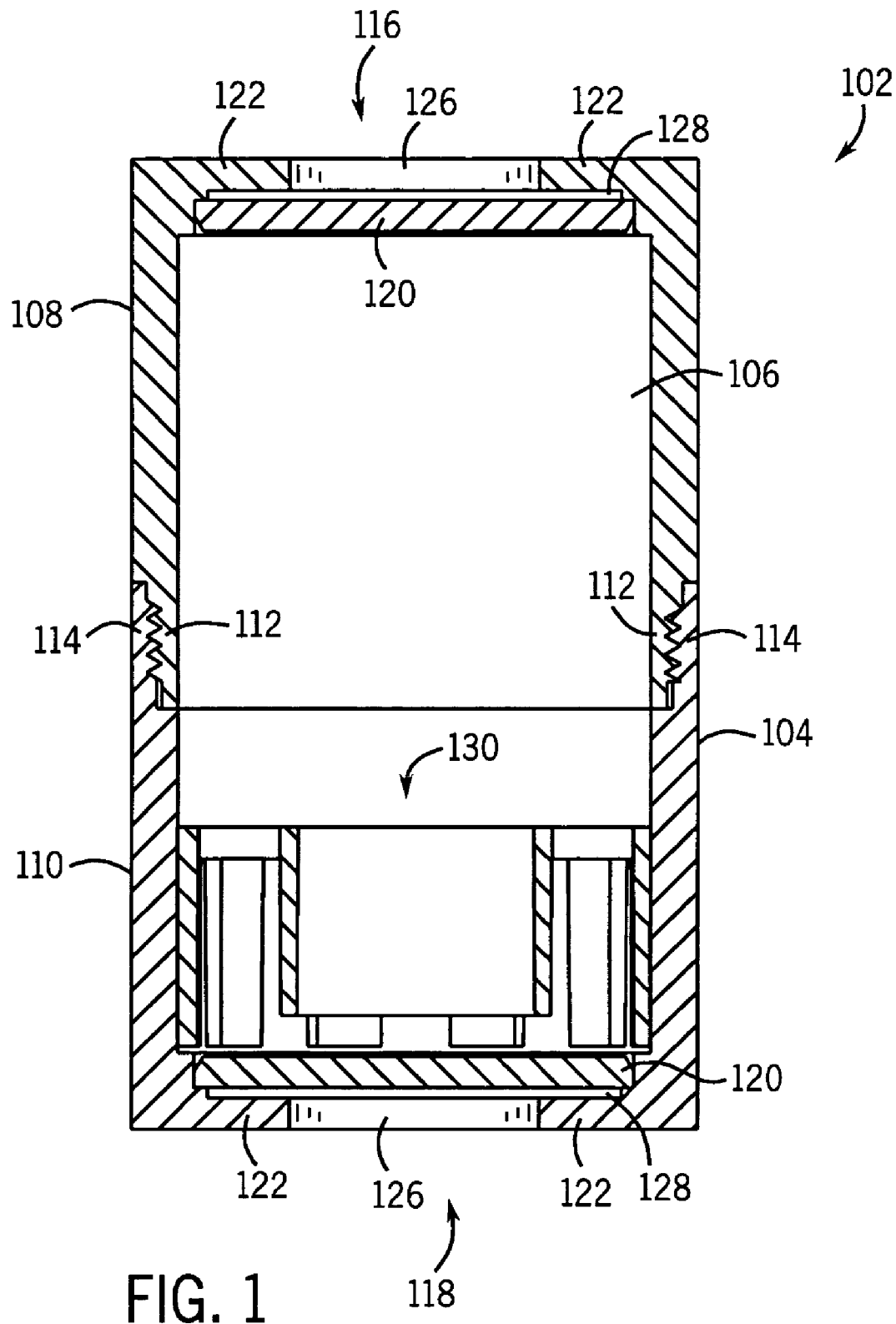
FIG. 1 is a representation of an exemplary implementation of an apparatus that comprises a radiation shielding container for one or more radioactive sources that comprises a top portion, a bottom portion, and a support component.
Figure 2:
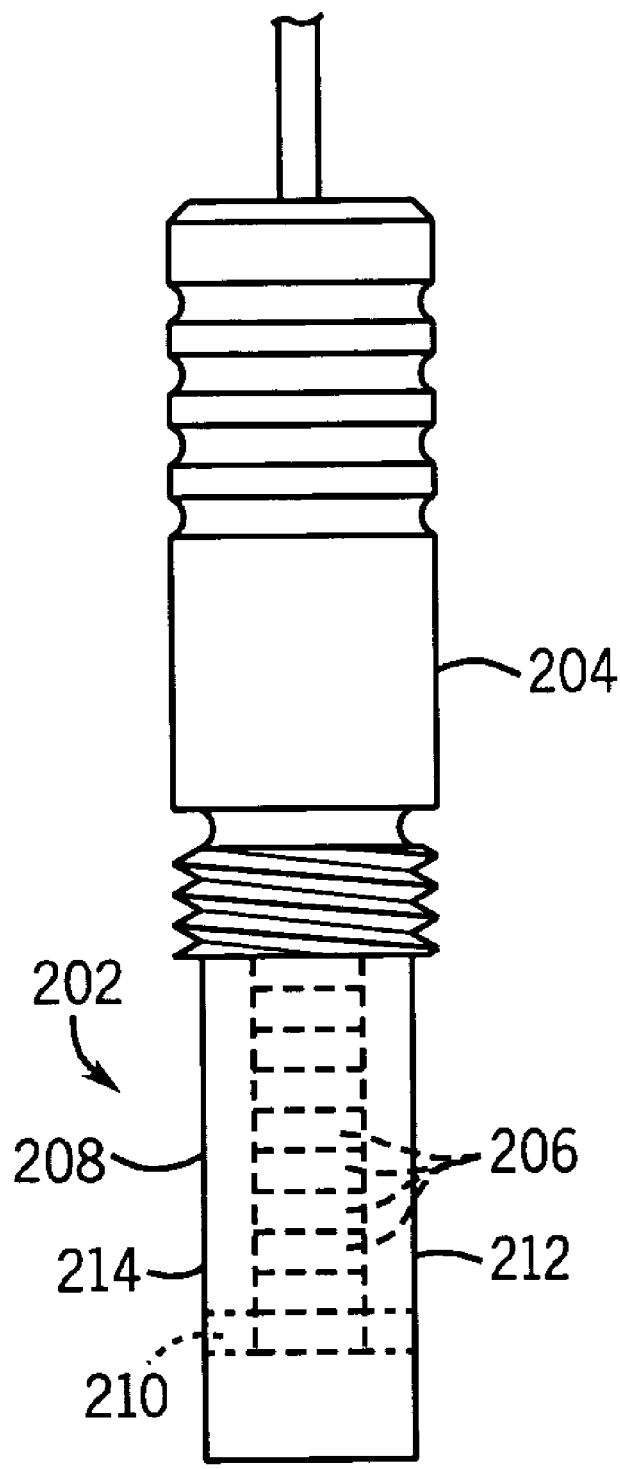
FIG. 2 is a representation of a cartridge that holds one or more of the one or more radioactive sources to be placed in the radiation shielding container of the apparatus of FIG. 1.

Turning to FIGS. 1–2, an apparatus 100 in one example comprises a plurality of components such as hardware components. A number of such components can be combined or divided in one example of the apparatus 100. The apparatus 100 in one example comprises any (e.g., horizontal, oblique, or vertical) orientation, with the description and figures herein illustrating one exemplary orientation of the apparatus 100, for explanatory purposes.

The apparatus 100 in one example comprises a radiation shielding container 102. The radiation shielding container 102 in one example encloses one or more radioactive sources 202. The radioactive sources 202 in one example comprise one or more radioactive seeds 206 contained within one or more cartridges 204. For example, the cartridges 204 comprise means for holding the radioactive seeds 206. The cartridges 204 may be magazines and/or containment components for the radioactive seeds 206.

The radiation shielding container 102 in one example comprises a container for shipping and/or storage of the radioactive sources 202. The radiation shielding container 102 may also be used for sterilization of the radioactive sources 202. For example, the radiation shielding container 102 may be used for sterilization of the radioactive sources 202 by sterilants, such as, steam sterilization, hydrogen peroxide sterilization, ethylene oxide sterilization, and/or gamma sterilization.

The radiation shielding container 102 in one example comprises a radiation resistant shell 104 and an internal chamber 106. The radiation resistant shell 104 shields an outer surface of the radiation shielding container 102 from radiation of the radioactive sources 202 that are within the internal chamber 106. For example, the radiation resistant shell 104 shields a user of the radiation shielding container 102 from a portion of the radiation of the radioactive sources 202.

The radiation shielding container 102 comprises a radiation shielding metal. For example, the radiation resistant shell 104 comprises stainless steel. If the radiation shielding container 102 comprises stainless steel, then the radiation shielding container 102 may be readily disposed or reused. For example, the radiation shielding container 102 does not need to be disposed as chemical waste. The radiation resistant shell 104 comprises a thickness that is sufficient to shield a user of the radiation shielding container 102 from radiation of the radioactive sources 202 that are within the internal chamber 106. For example, the thickness is sufficient to shield nuclides of the radioactive sources 202 used in brachytherapy, for example, Iodine-125 ("I-125") or Palladium-103 ("Pd-103"). The thickness of the radiation resistant shell 104 in one example is about three or four millimeters (⅛ inch).

Referring to FIGS. 1–6, the radiation resistant shell 104 in one example comprises a top portion 108 and a bottom portion 110. In one example, the top portion 108 comprises a cover to the bottom portion 110. For example, the top portion 108 comprises a lid to enclose the radioactive sources 202 in the internal chamber 106 within the bottom portion 110. In another example, the top portion 108 comprises a top half portion and the bottom portion 110 comprises a bottom half portion. For example, the top portion 108 and the bottom portion 108 comprise a substantially similar size.

Figure 3:
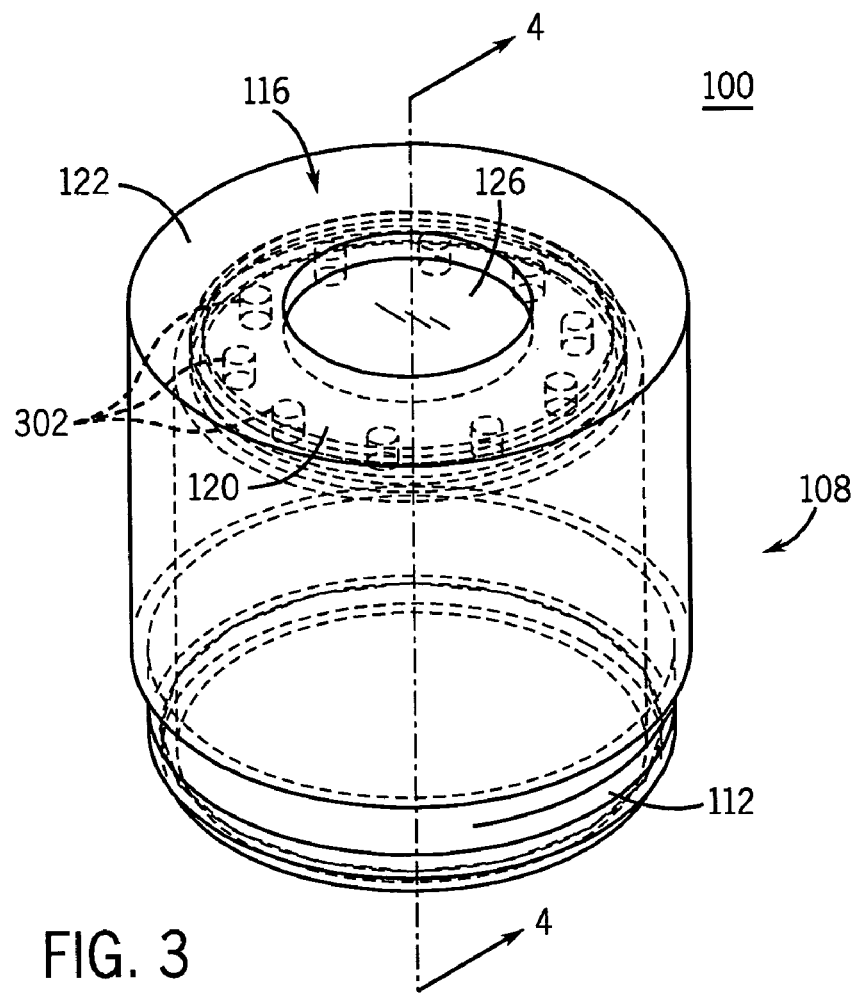
FIG. 3 is a perspective representation of the top portion of the radiation shielding container of the apparatus of FIG. 1, and illustrates in phantom an interior portion of the radiation shielding container.
Figure 4:
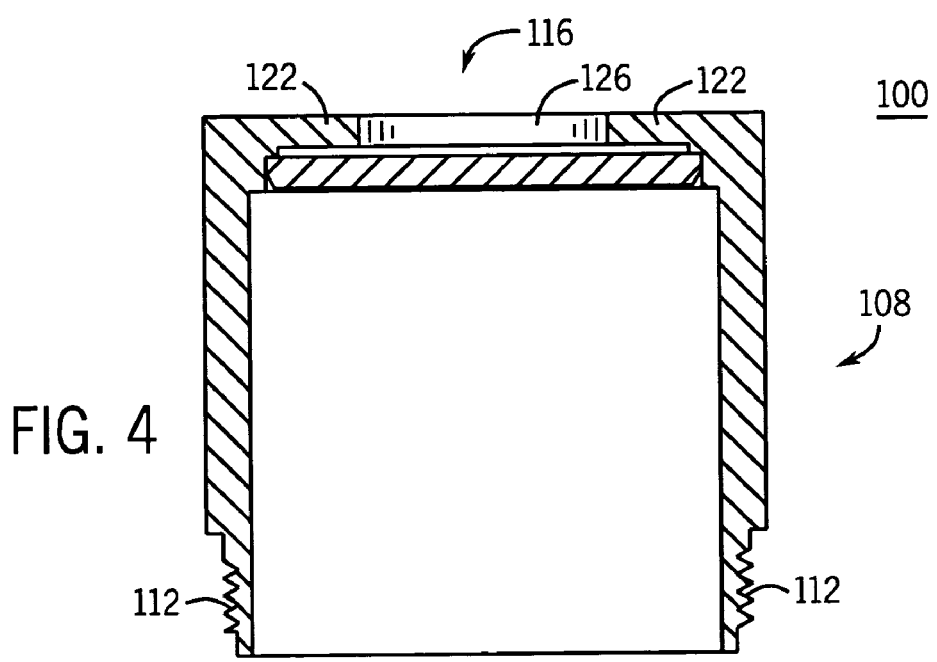
FIG. 4 is a sectional representation of the top portion of the radiation shielding container directed along line 4—4 of FIG. 3.
Figure 5:
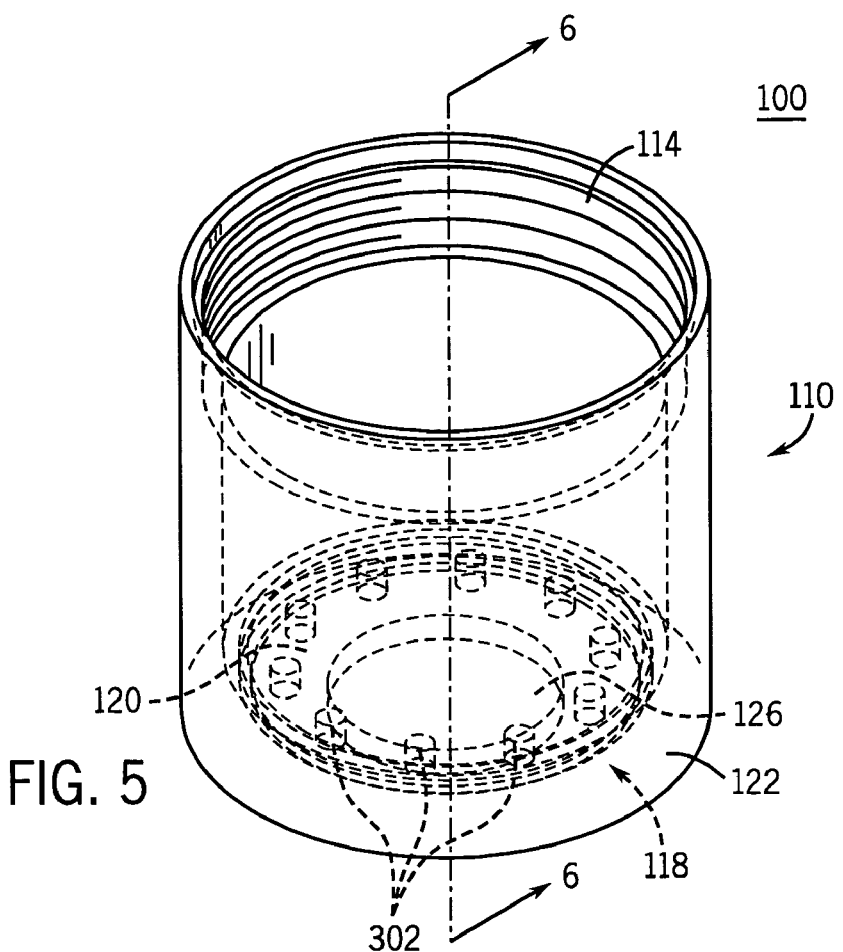
FIG. 5 is a perspective representation of the bottom portion of the radiation shielding container of the apparatus of FIG. 1, and illustrates in phantom an interior portion of the radiation shielding container.
Figure 6:
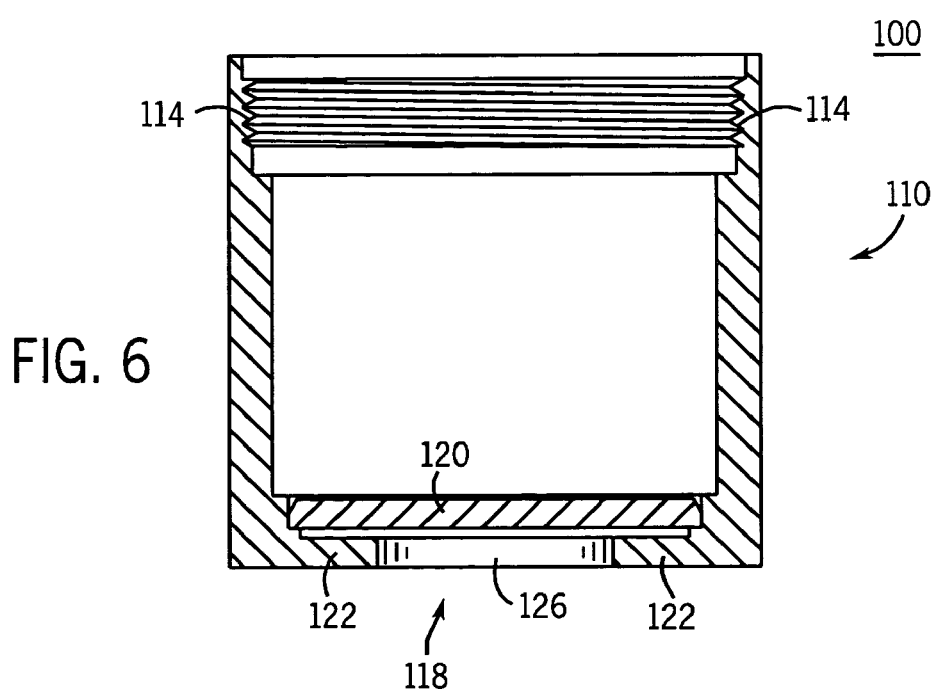
FIG. 6 is a sectional representation of the bottom portion of the radiation shielding container directed along line 6—6 of FIG. 5.

Referring to FIGS. 2–3 and 5, the top portion 108 and the bottom portion 110 are engageable and disengageable to selectively enclose the radioactive sources 202 within the internal chamber 106. In one example, the height of the radiation shielding container 102 is designed to hold one or more of the cartridges 204 of the radioactive seeds 206. In another example, the height of the radiation shielding container 102 is designed to hold a radioactive source of another height.

The top portion 108 and the bottom portion 110 employ a connection component to couple the top portion 108 with the bottom portion 110. For example, the connection component may be a bayonet connection, a screw cap connection, or a threaded connection. The top portion 108 in one example comprises a first threaded connection portion 112 and the bottom portion 110 comprises a second threaded connection portion 114. The first threaded connection portion 112 and the second threaded connection portion 114 engage to enclose the radioactive sources 202 within the radiation shielding container 102. For example, the first threaded connection portion 112 and the second threaded connection portion 114 screw together to connect the top portion 108 together with the bottom portion 110.

The radiation shielding container 102 comprises one or more vents 116 and 118. The vents 116 and 118 allow passage of a sterilant through the radiation shielding container 102. The sterilant in one example comprises a sterilization gas, such as steam. For example, the vents 116 and 118 allow passage of the steam through the internal chamber 106 for sterilization of the radioactive sources 202. The vents 116 and 118 allow sterilization of the radioactive sources 202 while the radioactive sources 202 are enclosed within the radiation shielding container 102. The radiation resistant shell 104 comprises one or more passages that form the one or more vents 116 and 118. The passages cause the sterilant to follow one or more tortuous paths between the internal chamber 106 and an exterior of the radiation shielding container 102. The vent 116 in one example comprises a tortuous path through the top portion 108. The vent 118 in one example comprises a tortuous path through the bottom portion 110.

The tortuous paths through the top portion 108 and the bottom portion 110 allow the passage of the sterilant into and out of the internal chamber 106. For example, one or more of the tortuous paths allow an entrance of the sterilant into the radiation shielding container 102 and one or more of the tortuous paths allow an exit of the sterilant from the radiation shielding container 102. However, the tortuous paths through the top portion 108 and the bottom portion 110 prevent passage of radiation from the radioactive sources 202 out of the internal chamber 106. For example, the tortuous paths through the top portion 108 and the bottom portion 110 are not direct line of sight paths for the radiation. The tortuous paths through the top portion 108 and the bottom portion 110 also prevent exit of one of the radioactive sources 202 from the internal chamber 106. For example, the size and shape of the openings in the vents 116 and 118 prevents exit of the radioactive sources 202 (e.g., the radioactive seeds 206) from the internal chamber 106. An individual radioactive seed of the radioactive seeds 206 is unable to pass through the vents 116 and 118. The vents 116 and 118 comprise indirect paths with one or more bends or turns. The vents 116 and 118 serve to prevent a direct line of sight between the radioactive sources 202 and a user of the radiation shielding container 102.

The vent 116 in one example is substantially similar to the vent 118. The vent 116 comprises a radiation resistant disk 120, a lip 122 of the radiation resistant shell 104, an opening 126 in the radiation resistant shell 104, and a space 128 between the radiation resistant disk 120 and the lip 122. The radiation resistant disk 120 is connected to the radiation resistant shell 104 at a position to leave the space 128 between the radiation resistant disk 120 and the lip 122.

The radiation resistant disk 120 comprises one or more holes 302. The holes 302 are aligned to be concealed under the lip 122 of the radiation resistant shell 104. For example, the lip 122 covers the holes 302 so that the sterilant that passes through the holes 302 does not have a direct path into or out of the internal chamber 106. Therefore, the vent 116 prevents the passage of radiation from the radioactive sources 202.

In one example, the vent 116 allows passage of the sterilant into the internal chamber 106. The sterilant is able to pass through the opening 126 in the radiation resistant shell 104 into the space 128. The sterilant then is able to pass around the lip 122 from the opening 126 to the space 128 under the lip 122. The sterilant is then able to pass through the holes 302 in the radiation resistant disk 120 and into the internal chamber 106.

In another example, the vent 116 allows passage of the sterilant out of the internal chamber 106. The sterilant is able to pass from the internal chamber 106 through the holes 302 in the radiation resistant disk 120 and into the space 128 under the lip 122. The sterilant then is able to pass around the lip 122 from the space 128 to the opening 126 in the radiation resistant shell 104. The sterilant is then released outside of the radiation shielding container 102.

Referring to FIGS. 1–2, the radioactive sources 202 in one example comprise radioactive seeds 206. The radioactive seeds 206 are used in radiation therapy to treat bodily cancers. For example, the radioactive seeds 206 comprise Iodine-125 or Palladium-103 seeds used in brachytherapy. A radioactive seed applicator in one example is used to inject the radioactive seeds 206 into afflicted tissue. The radioactive seeds 206 in one example are contained within one or more cartridges 204. The cartridge 204 engages with the radioactive seed applicator to transfer radioactive seeds 206 from the cartridge 204 to the radioactive seed applicator for insertion into the afflicted tissue.

Figure 9:
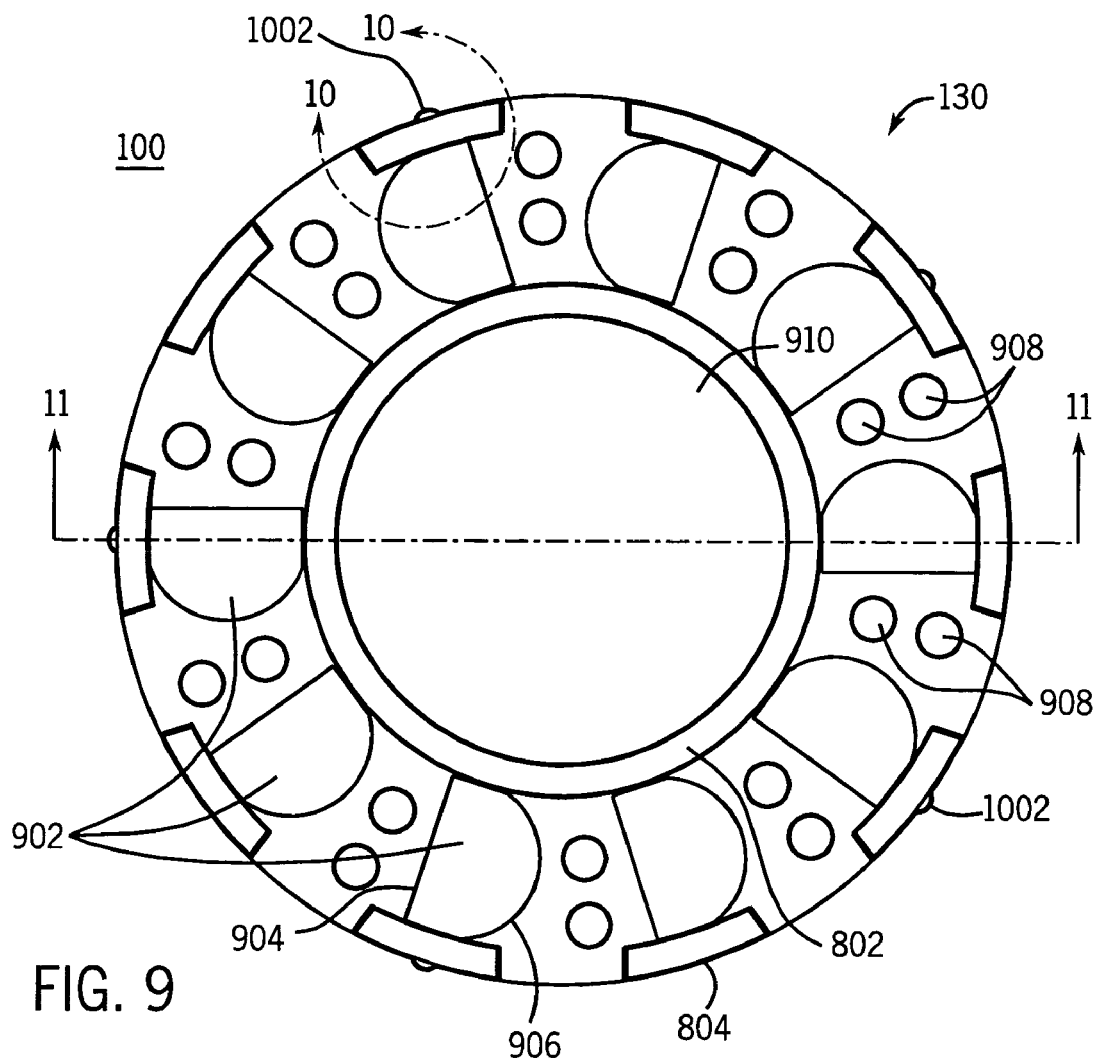
FIG. 9 is a top representation of the support component of the radiation shielding container of the apparatus of FIG. 7, and further illustrates one or more openings in the support component that serve to receive the one or more radioactive sources, one or more holes in the support component that serve to allow passage of sterilant therethrough, and one or more protruding ribs of the support component that serve to connect the support component with the radiation shielding container.
Figure 11:
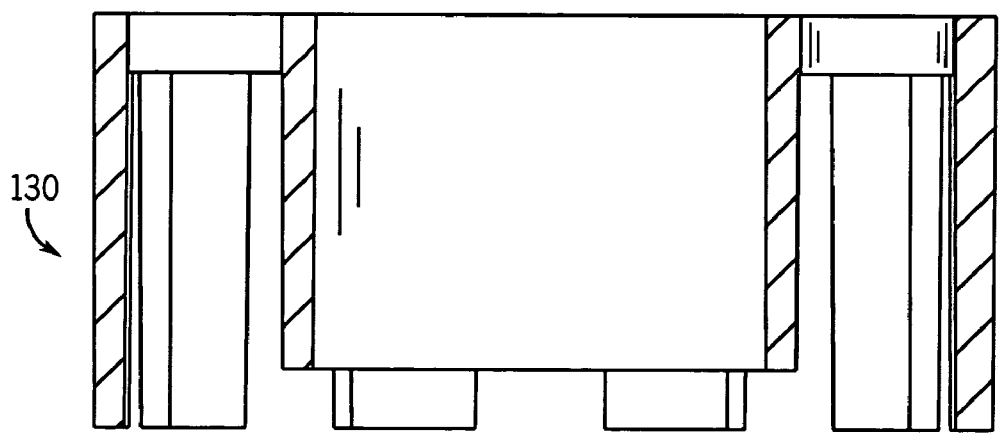
FIG. 11 is a sectional representation of the support component directed along line 11—11 of FIG. 10.

Referring to FIGS. 7–11, the radiation shielding container 102 (FIG. 1) comprises a storage and/or shipping container for the cartridges 204 (FIG. 2) that hold the radioactive seeds 206 (FIG. 2). The radiation shielding container 102 comprises a support component 130 that restrains movement within the radiation shielding container 102 of the cartridges 204. The support component 130 in one example is made of plastic. The plastic of the support component 130 in one example comprises substantially similar expansion properties as the stainless steel of the radiation resistant shell 104 (FIG. 1). The shape of the support component 130 is retained during sterilization of the radiation shielding container 102. For example, the plastic of the support component 130 may be autoclaved. Referring to FIGS. 9–10, the support component 130 in one example comprises an insert into the radiation resistant shell 104. The support component 130 is press-fit into the radiation resistant shell 104. The support component 130 in one example comprises one or more connection components that serve to prevent removal of the support component 130 from the radiation resistant shell 104. For example, the support component 130 comprises one or more protruding ribs 1002 on a side portion of the support component 130. The protruding ribs 1002 promote reduction in a relative movement between the support component 130 and the radiation resistant shell 104. For example, the protruding ribs 1002 crush down upon the press-fit of the support component 130 into the radiation resistant shell 104. The protruding ribs 1002 serve to prevent the removal of the support component 130 from the radiation resistant shell 104.

The tolerances of the support component 130 and the radiation resistant shell 104 are chosen so that the radiation resistant shell 104 may receive and hold the support component 130. For example, the support component 130 remains inside the radiation resistant shell 104 during use of the radiation shielding container 102. The protruding ribs 1002 of the support component 130 serve to prevent accidental detachment of the support component 130 from the radiation resistant shell 104 upon opening the radiation shielding container 102. If the support component 130 was easily removable from the radiation resistant shell 104, then a user of the radiation shielding container 102 may be tempted to remove the support component 130 with the radioactive sources 202 (FIG. 2) from the internal chamber 106 thus being exposed to radiation. In one example, an adhesive is used to attach the support component 130 with the radiation resistant shell 104.

Referring to FIG. 9, the support component 130 comprises one or more openings 902 of a size and shape to receive the radioactive sources 202. In one example, the size and shape of the openings 902 are designed to receive the cartridges 204 of radioactive seeds 206. In another example, the size and shape of the openings 902 are designed to receive radioactive sources 202 of another size and shape. The openings 902 in the support component 130 in one example receives a lower portion 208 of the cartridges 204. The lower portion 208 of the cartridges 204 in one example comprises a flat side portion and curved side portion. The openings 902 in the support component 130 comprise a flat side portion 904 and a curved side portion 906 with a substantially similarly shape as the lower portion 208 of the cartridges 204.

The openings 902 in the support component 130 are shaped to uniquely receive the one or more cartridges 204. For example, due to the shape of the lower portion 208 of the cartridges 204 and the shape of the openings 902 in the support component 130, the cartridges 204 are fully seated on the support component 130 when the cartridges 204 are aligned to match the flat side portion 904 and a curved side portion 906 of the openings 902 in the support component 130. The openings 902 on the support component 130 are shaped to prevent a rotation of the cartridges 204 within the one or more openings 902. The support component 130 holds the cartridges 204 in place within the radiation shielding container 102 and also holds the radioactive seeds 206 within the cartridges 204.

Referring to FIGS. 2 and 8, the cartridges 204 comprise one or more exit holes for the radioactive seeds 206 on one or more sides of the cartridge 204. For example, the cartridge 204 comprises an exit path 210 for the radioactive seeds 206. The exit path 210 passes through the cartridge 204 from a first side 212 of the cartridge 204 to a second side 214 of the cartridge 204. During use of the cartridge 204 the radioactive seeds 206 are released from the cartridge 204 through the exit path 210. While the cartridge 204 is within the radiation shielding container 102, the radioactive seeds 206 should remain in the cartridge 204. Therefore, the support component 130 serves to prevent a release of one or more of the radioactive seeds 206 from the cartridge 204.

The support component 130 abuts the first side 212 and the second side 214 of the cartridge 204 to cover the exit path 210 in the cartridge 204. The support component 130 comprises one or more inner flanges 802 and one or more outer flanges 804. The inner flange 802 in one example abuts the first side 212 of the cartridge 204 to cover a first side of the exit path 210 in the cartridge 204. The outer flange 804 in one example abuts the second side 214 of the cartridge 204 to cover a second side of the exit path 210 in the cartridge 204. For example, the cartridge 204 is housed in the support component 130 between the inner flange 802 and the outer flange 804.

Referring to FIG. 9, the support component 130 comprises one or more holes 908 to allow passage of the sterilant through the support component 130. The holes 908 direct a flow of the sterilant past the radioactive sources 202. For example, the holes 908 direct the sterilant past the radioactive seeds 206 that are contained within the cartridges 204. The holes 908 promote the flow of the sterilant against the radioactive sources 202 through the support component 130 rather than passing through an opening 910 in the middle of the support component 130. The sterilant that passes through the holes 908 passes closer to the radioactive sources 202 than the sterilant that passes through the opening 910.

The opening 910 in one example receives a vial for storage of one or more radioactive sources 202. For example, the vial holds one or more extra radioactive seeds (e.g., analogous to the radioactive seeds 206). In one example, the vial stores the extra radioactive seeds that are unused after the brachytherapy procedure. In another example, the vial stores the extra radioactive seeds that are shipped along with the cartridges 204 that hold the radioactive seeds 206. The radiation shielding container 102 comprises a buffer layer between the support component 102 and the vial. The buffer layer in one example comprises a compliant pad, for example, a foam material. The buffer layer restrains movement within the radiation shielding container 102 of the vial. For example, the buffer layer prevents direct contact between the support component 130 and the vial.

Referring to FIGS. 1–2, an illustrative description of one exemplary operation of the apparatus 100 is now presented, for explanatory purposes. The radiation shielding container 102 in one example comprises a shipping container for the radioactive sources 202. For example, the cartridges 204 that hold one or more radioactive seeds 206 may be shipped in the radiation shielding container 102. In another example, the radiation shielding container 102 may be used for storage of the cartridges 204.

The cartridges 204 are packed into the support component 130 to restrain a movement of the cartridges 204. For example, the cartridges 204 are placed into the openings 902 in the support component 130. A foam pad is placed between the top of the cartridges 204 and the radiation resistant shell 104 to prevent contact between the cartridges 204 and the radiation resistant shell 104. Then, the top portion 108 and the bottom portion 110 of the radiation resistant shell 104 are connected to enclose the cartridges 204 within a radiation shielded cavity between the top portion 108 and the bottom portion 110 inside the radiation resistant shell 104. The radiation shielding container 102 may be shipped to a physician for use in a brachytherapy procedure.

Upon receipt of the radiation shielding container 102, the physician may sterilize the radioactive sources 202 in the radiation shielding container 102 by passing the sterilant through the radiation shielding container 102. For example, the radiation shielding container 102 may be placed into an autoclave for sterilization. Steam from the autoclave may flow into the internal chamber 106 of the radiation shielding container 102 through one or more of the vents 116 and 118. Once the radioactive sources 202 are sterilized they may be used for the brachytherapy procedure. After use of the radioactive sources 202 that came in the radiation shielding container 102, the radiation shielding container 102 is able to be reused for containment of one or more other radioactive sources (e.g., analogous to the radioactive sources 202). For example, the radiation shielding container 102 is able to store or ship the other radioactive sources.

The steps or operations described herein are just exemplary. There may be many variations to these steps or operations without departing from the spirit of the invention. For instance, the steps may be performed in a differing order, or steps may be added, deleted, or modified.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An apparatus, comprising:
    a radiation shielding container for storage of one or more seed cartridges that hold one or more radioactive seeds, wherein the one or more seed cartridges are inaccessible for attachment to a radioactive seed applicator while being stored within the radiation shielding container;
    wherein the radiation shielding container comprises a support component that restrains movement within the radiation shielding container of one or more of the one or more seed cartridges;
    wherein the radiation shielding container comprises one or more vents for movement of a sterilant therethrough.

2. The apparatus of claim 1, wherein the radiation shielding container comprises a stainless steel shell and an internal chamber therein that stores the one or more seed cartridges that hold the one or more radioactive seeds.

3. The apparatus of claim 2, wherein the stainless steel shell serves to shield a user of the radiation shielding container from radiation from the one or more radioactive seeds.

4. The apparatus of claim 1, wherein the radiation shielding container comprises a first portion and a second portion; wherein the first portion and the second portion are engageable to enclose the one or more seed cartridges that hold the one or more radioactive seeds therein.

5. The apparatus of claim 4, wherein the first portion comprises a first threaded connection portion and the second portion comprise a second threaded connection portion; wherein the first threaded connection portion and the second threaded connection portion are engageable and disengageable for selective enclosure within the radiation shielding container of the one or more seed cartridges that hold the one or more radioactive seeds.

6. The apparatus of claim 1, wherein the radiation shielding container comprises an internal chamber that stores the one or more seed cartridges that hold the one or more radioactive seeds, wherein the radiation shielding container comprises one or more passages that form the one or more vents; wherein the one or more passages cause the sterilant to follow one or more tortuous paths between the internal chamber and an exterior of the radiation shielding container.

7. The apparatus of claim 6, wherein the one or more tortuous paths allow the passage of the sterilant into the internal chamber but prevent passage of radiation from the one or more radioactive seeds out of the internal chamber.

8. The apparatus of claim 1, wherein the radiation shielding container is able to be autoclaved for sterilization of the one or more radioactive seeds; wherein the sterilant comprises steam, wherein the one or more vents allow passage of steam into the radiation shielding container, past the one or more radioactive seeds, and then out of the radiation shielding container.

9. The apparatus of claim 1, wherein an opening size of the one or more vents allows the passage of the sterilant into the radiation shielding container but prevents an exit of one of the one or more radioactive seeds from the radiation shielding container.

10. The apparatus of claim 1, wherein the one or more vents comprise a first vent and a second vent; wherein during sterilization of the radiation shielding container, one or more of the first vent and the second vent allow an entrance of the sterilant into the radiation shielding container and one or more of the first vent and the second vent allow an exit of the sterilant from the radiation shielding container.

11. The apparatus of claim 10, wherein the radiation shielding container comprises a cylinder with a bottom end portion and a top end portion; wherein the first vent passes through the bottom end portion of the radiation shielding container, wherein the second vent passes through the top end portion of the radiation shielding container.

12. The apparatus of claim 1, wherein the radiation shielding container comprises a shipping container for the one or more seed cartridges that hold the one or more radioactive seeds.

13. The apparatus of claim 1, wherein the one or more seed cartridges comprise radioactive seed cartridges employable with the radioactive seed applicator to insert one or more of the one or more radioactive seeds into a patient; wherein the support component comprises one or more openings of a size and shape to receive the one or more radioactive seed cartridges.

14. The apparatus of claim 13, wherein the one or more openings comprise a flat portion and a curved portion to receive a substantially similar shaped flat portion and curved portion of the one or more radioactive seed cartridges.

15. The apparatus of claim 1, wherein the support component comprises one or more openings that comprise a shape that serves to uniquely receive the one or more seed cartridges.

16. The apparatus of claim 1, wherein the support component comprises one or more openings that comprise a shape that serves to prevent a rotation of the one or more seed cartridges within the one or more openings.

17. The apparatus of claim 1, wherein the one or more seed cartridges comprise a seed cartridge that holds the one or more radioactive seeds, wherein the seed cartridge comprises an exit hole for the one or more radioactive seeds on a side of the seed cartridge; wherein the support component abuts the side of the seed cartridge to cover the exit hole.

18. The apparatus of claim 17, wherein the support component serves to prevent a release of one or more of the one or more radioactive seeds from the seed cartridge.

19. The apparatus of claim 1, wherein the one or more seed cartridges comprise a seed cartridge that holds the one or more radioactive seeds, wherein the seed cartridge comprises an exit path for the one or more radioactive seeds, wherein the exit path passes through the seed cartridge from a first side of the seed cartridge to a second side of the seed cartridge; wherein a first portion of the support component abuts a first side of the seed cartridge to cover a first side of the exit path in the seed cartridge; wherein a second portion of the support component abuts a second side of the seed cartridge to cover a second side of the exit path in the seed cartridge.

20. The apparatus of claim 19, wherein the first portion of the support component comprises an inner flange of the support component and the second portion of the support component comprises an outer flange of the support component; wherein the seed cartridge is removably contained between the inner flange and the outer flange.

21. The apparatus of claim 1, wherein the support component comprises one or more holes that allow for passage of the sterilant through the support component.

22. The apparatus of claim 21, wherein the one or more holes pass through the support component at a location that directs a flow of the sterilant past the one or more of the one or more radioactive seeds that are held within the one or more seed cartridges.

23. The apparatus of claim 1, wherein a shape of the support component is retained during sterilization of the radiation shielding container.

24. The apparatus of claim 1, wherein the support component comprises a plastic insert that may be autoclaved.

25. The apparatus of claim 1, wherein the support component comprises an opening for a vial, wherein the vial may store one or more additional radioactive sources.

26. The apparatus of claim 25, wherein the radiation shielding container comprises a buffer layer between the support component and the vial that restrains movement within the radiation shielding container of the vial.

27. The apparatus of claim 1, wherein the support component comprises an insert that is press-fit into the radiation shielding container; wherein once the support component is press-fit into the radiation shielding container, the support component remains within the radiation shielding container.

28. The apparatus of claim 27, wherein the support component comprises one or more connection components that serve to prevent removal of the support component from the radiation shielding container.

29. The apparatus of claim 27, wherein the support component comprises one or more protruding ribs on a side portion of the support component;
   wherein the one or more protruding ribs promote a reduction in a relative movement between the support component and the radiation shielding container;
   wherein the one or more protruding ribs serve to prevent the removal of the support component from the radiation shielding container.

30. The apparatus of claim 1, wherein the support component comprises an insert that is coupled with the radiation shielding container, wherein attachment between the support component and the radiation shielding container serves to prevent a relative movement between the support component and the radiation shielding container.

31. The apparatus of claim 1, wherein the radiation shielding container comprises a stainless steel shell, wherein the stainless steel shell comprises a thickness to shield nuclides used in brachytherapy.

32. The apparatus of claim 1, wherein the radiation shielding container comprises a first portion and a second portion;
   wherein the first portion and the second portion are engageable to enclose the one or more seed cartridges that hold the one or more radioactive seeds therein;
   wherein the vents allow sterilization of the one or more radioactive seeds while the one or more seed cartridges that hold the one or more radioactive seeds are enclosed within the radiation shielding container.

33. An apparatus, comprising:
   a radiation shielding container for of one or more radioactive seed cartridges, wherein the one or more radioactive seed cartridges are inaccessible for attachment to a radioactive seed applicator while being stored within the radiation shielding container;
   wherein the radiation shielding container comprises a support component, wherein the support component comprises one or more openings to receive the one or more radioactive seed cartridges;
   wherein the radiation shielding container comprises an internal chamber that contains the support component and the one or more radioactive seed cartridges, wherein the one or more radioactive seed cartridges within the radiation shielding container are able to be sterilized in an autoclave;
   wherein the radiation shielding container comprises one or more passages that cause steam from the autoclave to follow one or more tortuous paths into the radiation shielding container to sterilize the one or more radioactive seed cartridges within the internal chamber.

34. The apparatus of claim 33, wherein the radiation shielding container comprises a stainless steel shell, wherein the stainless steel shell shields the outer surface of the stainless steel shell from radiation of the one or more radioactive seed cartridges.

35. The apparatus of claim 33, wherein the radiation shielding container comprises a first portion and a second portion, wherein the first portion comprises a first threaded connection portion and the second portion comprise a second threaded connection portion;
   wherein the first threaded connection portion and the second threaded connection portion are engageable to enclose the one or more radioactive seed cartridges therein.

36. The apparatus of claim 33, wherein the one or more tortuous paths allow the steam into the internal chamber but prevent passage of radiation from the one or more radioactive seed cartridges out of the internal chamber.

37. The apparatus of claim 33, wherein the one or more radioactive seed cartridges hold one or more radioactive seeds;
   wherein an opening size of the one or more passages allows the steam into the internal chamber but prevents an exit of one of the one or more radioactive seeds from the internal chamber.

38. The apparatus of claim 33, wherein the one or more tortuous paths comprise a first tortuous path and a second tortuous path;
   wherein during sterilization of the radiation shielding container, one or more of the first tortuous path and the second tortuous path allows an entrance of the steam into the internal chamber and one or more of the first tortuous path and the second tortuous path allows an exit of the steam from the internal chamber.

39. The apparatus of claim 33, wherein the radiation shielding container comprises a shipping container for the one or more radioactive seed cartridges.

40. The apparatus of claim 33, wherein the one or more radioactive seed cartridges hold one or more radioactive seeds, wherein the one or more radioactive seed cartridges are employable with the radioactive seed applicator to insert one or more of the one or more radioactive seeds into a patient;
   wherein the support component comprises one or more openings of a size and shape to receive the one or more radioactive seed cartridges.

41. The apparatus of claim 33, wherein the one or more radioactive seed cartridges comprise a radioactive seed cartridge that holds one or more radioactive seeds, wherein the radioactive seed cartridge comprises an exit path for the one or more radioactive seeds, wherein the exit path passes through the radioactive seed cartridge from a first side of the radioactive seed cartridge to a second side of the radioactive seed cartridge;
   wherein a first portion of the support component abuts a first side of the radioactive seed cartridge to cover a first side of the exit path in the radioactive seed cartridge;
   wherein a second portion of the support component abuts a second side of the radioactive seed cartridge to cover a second side of the exit path in the radioactive seed cartridge.

42. The apparatus of claim 33, wherein the support component comprises one or more holes that allow for passage of the steam therethrough.

43. The apparatus of claim 33, wherein the support component comprises an insert that is press-fit into the internal chamber of the radiation shielding container,
   wherein once the support component is press-fit into the internal chamber of the radiation shielding container, the support component remains within the internal chamber of the radiation shielding container.

44. The apparatus of claim 43, wherein the support component comprises one or more protruding ribs on a side portion of the support component;
   wherein the one or more protruding ribs promote a reduction in a relative movement between the support component and the radiation shielding container;

wherein the one or more protruding ribs serve to prevent a removal of support component from the radiation shielding container.

45. The apparatus of claim 33, wherein the radiation shielding container comprises a stainless steel shell, wherein the stainless steel shell comprises a thickness to shield nuclides used for brachytherapy.

46. A radiation shielding container for one or more radioactive seeds, comprising:
   means for restraining movement within the radiation shielding container of one or more seed cartridges that hold one or more of the one or more radioactive seeds, wherein the one or more seed cartridges are inaccessible for attachment to a radioactive seed applicator while being stored within the radiation shielding container; and
   means for allowing passage of sterilant into the radiation shielding container.

47. The radiation shielding container of claim 46, wherein the means for allowing passage of the sterilant serves to prevent passage of radiation from the one or more radioactive seeds out of the radiation shielding container.

48. The radiation shielding container of claim 46, wherein the means for restraining movement comprises means for preventing removal from the radiation shielding container.

49. The radiation shielding container of claim 46, wherein the means for allowing passage of sterilant comprises means for allowing sterilization of the one or more radioactive seeds within the radiation shielding container.

50. A method, comprising the steps of:
   shipping one or more seed cartridges that hold one or more radioactive seeds in a radiation shielding container that comprises:
      one or more vents for movement of a sterilant therethrough for sterilization of the one or more radioactive seeds; and
      a support component that restrains movement within the radiation shielding container of one or more of the one or more seed cartridges;
   wherein the one or more seed cartridges are inaccessible for attachment to a radioactive seed applicator while being stored within the radiation shielding container.

51. The method of claim 50, wherein the step of shipping the one or more seed cartridges that hold the one or more radioactive seeds in the radiation shielding container that comprises the one or more vents that allow passage of the sterilant therethrough for sterilization of the one or more radioactive seeds comprises the step of:
   packing the one or more seed cartridges into the support component within the radiation shielding container to restrain the movement of the one or more of the one or more seed cartridges.

52. The method of claim 50, wherein the step of packing the one or more seed cartridges into the support component within the radiation shielding container to restrain the movement of the one or more of the one or more seed cartridges comprises the step of:
   inserting the one or more seed cartridges into one or more openings adapted to receive the one or more seed cartridges in the support component.

53. The method of claim 50, further comprising the step of:
   connecting a first end portion of the radiation shielding container with a second end portion of the radiation shielding container to selectively enclose the one or more seed cartridges in a radiation shielded cavity between the first end portion and the second end portion.

54. A method, comprising the steps of:
   receiving a radiation shielding shipping container of one or more seed cartridges that hold one or more radioactive seeds, wherein the one or more seed cartridges are inaccessible for attachment to a radioactive seed applicator while being stored within the radiation shielding shipping container, wherein the radiation shielding shipping container comprises a support component that restrains movement within the radiation shielding container of one or more of the one or more seed cartridges, wherein the radiation shielding shipping container comprises, one or more vents for movement of a sterilant therethrough; and
   sterilizing the one or more radioactive seeds within the radiation shielding shipping container by passing the sterilant into the radiation shielding shipping container through one or more of the one or more vents.

55. The method of claim 54, wherein the radiation shielding shipping container comprises one or more passages that form the one or more vents, wherein the one or more passages cause the sterilant to follow one or more tortuous paths between the internal chamber and an exterior of the radiation shielding container, wherein the sterilant comprises steam, wherein the step of sterilizing the one or more radioactive seeds in the radiation shielding shipping container by passing the sterilant into one or more of the one or more vents comprises the step of:
   autoclaving the radiation shielding shipping container to pass the steam, for sterilization of the one or more radioactive seeds, into the radiation shielding shipping container through one or more of the one or more tortuous paths and then out of one or more of the one or more tortuous paths.

56. The method of claim 54, wherein the one or more radioactive seeds comprise one or more first radioactive seeds, the method further comprising the step of:
   reusing the radiation shielding shipping container for one or more second radioactive seeds.

57. An apparatus, comprising:
   a radiation shielding container; and
   one or more seed cartridges that hold radioactive seeds;
   wherein the one or more seed cartridges are inaccessible for attachment to a radioactive seed applicator while being stored within the radiation shielding container;
   wherein the radiation shielding container comprises a support component that receives the one or more seed cartridges and restrains movement within the radiation shielding container of the one or more seed cartridges;
   wherein the radiation shielding container comprises one or more vents for movement of a sterilant therethrough.

58. The apparatus of claim 57, wherein the support component comprises an insert that is press-fit into the radiation shielding container.

59. The apparatus of claim 1, wherein the radiation shielding container comprises an inner chamber that fully contains the one or more seed cartridges, wherein the radiation shielding container prevents the one or more seed cartridges from attaching to the radioactive seed applicator while the one or more seed cartridges are stored within the radiation shielding container;
   wherein the one or more seed cartridges are removed from the radiation shielding container for attachment to the radioactive seed applicator.

60. The apparatus of claim 1, wherein the radiation shielding container comprises a top portion and a bottom portion that are engageable to enclose a plurality of seed cartridges, wherein the support component is located in the bottom portion;

wherein the support component comprises a top surface and one or more portions that extend down from the top surface to couple the support component into the bottom portion, wherein the top surface comprises a plurality of openings to receive the plurality of seed cartridges.

61. The apparatus of claim 60, wherein the top surface comprises the plurality of openings to receive the plurality of seed cartridges and a plurality of holes that allow for passage of the sterilant through the support component;

wherein the plurality of openings are aligned relative to the plurality of holes so that the sterilant flows against a side of the one or more radioactive seeds that are held within the plurality of seed cartridges;

wherein the plurality of openings comprise a shape that serves to engage the plurality of seed cartridges to prevent a rotation of the plurality of seed cartridges within the plurality of openings.

62. The apparatus of claim 61, wherein the plurality of openings comprise an opening for a seed cartridge of the plurality of seed cartridges;

wherein the plurality of holes comprise a first plurality of holes on a first side of the opening for movement of the sterilant against a first side of the seed cartridge, wherein the plurality of holes comprise a second plurality of holes on a second side of the opening for movement of the sterilant against a second side of the seed cartridge.

* * * * *